(12) United States Patent
Kato et al.

(10) Patent No.: US 9,052,279 B2
(45) Date of Patent: Jun. 9, 2015

(54) GAS SENSOR APPARATUS AND METHOD FOR CONTROLLING THE SAME

(75) Inventors: Tsuyoshi Kato, Kounan (JP); Kentaro Mori, Nagoya (JP); Soichi Kawaguchi, Inazawa (JP); Yoshinori Hibino, Kasugai (JP); Ryosuke Ichida, Komaki (JP)

(73) Assignee: NGK SPARK PLUG CO., LTD., Aichi (JP)

(*) Notice: Subject to any disclaimer, the term of this patent is extended or adjusted under 35 U.S.C. 154(b) by 497 days.

(21) Appl. No.: 13/458,312

(22) Filed: Apr. 27, 2012

(65) Prior Publication Data

US 2012/0273369 A1 Nov. 1, 2012

(30) Foreign Application Priority Data

Apr. 28, 2011 (JP) ................................. 2011-101967

(51) Int. Cl.
*G01N 27/406* (2006.01)
*F02D 41/14* (2006.01)

(52) U.S. Cl.
CPC ........ *G01N 27/4067* (2013.01); *F01N 2560/20* (2013.01); *F02D 41/1454* (2013.01); *F02D 41/1494* (2013.01); *F02D 41/1495* (2013.01)

(58) Field of Classification Search
CPC ............ G01N 27/4067; G01N 27/407; G01N 27/409; F01N 2560/20; F01N 2560/025
See application file for complete search history.

(56) References Cited

U.S. PATENT DOCUMENTS

| | | | |
|---|---|---|---|
| 5,852,228 A | 12/1998 | Yamashita et al. | |
| 5,974,857 A | 11/1999 | Yamashita et al. | |
| 6,550,305 B2 * | 4/2003 | Tomisawa | 73/1.06 |
| 6,649,041 B2 * | 11/2003 | Hashimoto et al. | 205/785 |
| 2002/0179594 A1 | 12/2002 | Hada et al. | |
| 2005/0205550 A1 | 9/2005 | Saito et al. | |
| 2006/0047468 A1 | 3/2006 | Aoki | |
| 2007/0010932 A1 | 1/2007 | Gotoh et al. | |
| 2007/0012564 A1 | 1/2007 | Hayashi et al. | |
| 2008/0116071 A1 | 5/2008 | Nakamura et al. | |
| 2008/0196489 A1 | 8/2008 | Fukagai et al. | |
| 2008/0196490 A1 | 8/2008 | Fukagai et al. | |

(Continued)

FOREIGN PATENT DOCUMENTS

| | | |
|---|---|---|
| CN | 1673728 A | 9/2005 |
| CN | 1701231 A | 11/2005 |

(Continued)

OTHER PUBLICATIONS

Communication dated Aug. 20, 2014, issued by the State Intellectual Property Office of the People's Republic of China in corresponding Chinese Application No. 201210134604.6.

*Primary Examiner* — Alexander Noguerola
(74) *Attorney, Agent, or Firm* — Sughrue Mion, PLLC

(57) ABSTRACT

When a detection signal obtained from the cell of a gas sensor (S15) has reached a start determination value (specifically, when the output voltage of the cell is higher than 600 mV (S16: YES) or lower than 300 mV (S17: YES)), a pulse voltage is applied to the cell (S18), and a start-time internal resistance is obtained on the basis of the detection signal having changed as a result of application of the pulse voltage (S20). The start-time internal resistance is compared with a deterioration determination value set in advance (S21). A target resistance of the cell used in temperature control (energization control) for the heater is corrected in accordance with the result of the comparison (S28). Thus, the temperature of the cell can be stably maintained constant irrespective of deterioration of the cell.

4 Claims, 4 Drawing Sheets

(56) References Cited

U.S. PATENT DOCUMENTS

| | | |
|---|---|---|
| 2010/0108540 A1 | 5/2010 | Kato et al. |
| 2014/0048415 A1 | 2/2014 | Kato et al. |

FOREIGN PATENT DOCUMENTS

| | | |
|---|---|---|
| CN | 101107513 A | 1/2008 |
| CN | 101251051 A | 8/2008 |
| CN | 101251053 A | 8/2008 |
| CN | 101738426 A | 6/2010 |
| JP | 06347437 A | 12/1994 |
| JP | 10-026599 A | 1/1998 |
| JP | 2006-300625 A | 11/2006 |
| JP | 2009-2810 A | 1/2009 |

\* cited by examiner

GAS SENSOR APPARATUS AND METHOD FOR CONTROLLING THE SAME

TECHNICAL FIELD

The present invention relates to a gas sensor apparatus which includes a gas sensor and which is used to perform air-fuel-ratio feedback control for an internal combustion engine, and to a method of controlling the gas sensor apparatus.

BACKGROUND ART

A known gas sensor for detecting the concentration of a specific gas such as oxygen includes at least one cell composed of a solid electrolyte member and a pair of electrodes. When the temperature of the solid electrolyte member rises, the solid electrolyte member becomes active, and an electromotive force is produced between the two electrodes in accordance with the difference in oxygen concentration between two atmospheres separated by the solid electrolyte member. The solid electrolyte member is heated by the heat of exhaust gas discharged from an internal combustion engine; however, in some cases, a heater is provided so as to quickly activate the solid electrolyte member. Also, since the internal resistance of the cell has a correlation with its temperature, the temperature control of the heater is performed through feedback control based on the internal resistance of the cell (see, for example, Patent Document 1). In the apparatus disclosed in Patent Document 1, electric power is supplied to the heater such that the internal resistance of the cell coincides with a target resistance, whereby the cell is maintained at a constant or fixed temperature.

Incidentally, it has been known that when the cell deteriorates because of, for example, elapse of time, the internal resistance changes. Even when the cell deteriorates, the cell can be maintained at the constant temperature by, for example, changing the target resistance in accordance with the degree of deterioration of the cell. The apparatus disclosed in Patent Document 1 utilizes the phenomenon that, when the cell deteriorates and its internal resistance changes, the electric power supplied to the heater changes. When the electric power supplied to the heater exceeds a predetermined level, the cell is determined to have deteriorated, and the target resistance is changed to a target resistance corresponding to the degree of deterioration.

PRIOR ART DOCUMENT

Patent Document

[Patent Document 1] Japanese Patent Application Laid-Open (kokai) No. H10-26599

SUMMARY OF THE INVENTION

Problems to be Solved by the Invention

However, in the case of the apparatus disclosed in Patent Document 1, the determination as to whether or not the cell has deteriorated (hereinafter referred to as "deterioration determination for the cell") cannot be performed until the cell is activated to a sufficient degree such that the internal resistance of the cell has a correlation with its temperature. In addition, the cell deterioration determination cannot be started until a long time elapses after startup of an engine. Moreover, since deterioration of the cell is not determined directly but is determined indirectly on the basis of the electric power supplied to the heater, the conventional apparatus has a problem in that the accuracy of deterioration detection is poor.

The present invention has been accomplished in order to solve the above-described problem, and its object is to provide a gas sensor apparatus which can start deterioration determination for a cell at an early timing and can perform the deterioration determination for the cell accurately, and a method of controlling the gas sensor apparatus.

Means for Solving the Problems

According to a first mode of the present invention, there is provided a gas sensor apparatus which includes a gas sensor having at least one cell composed of a solid electrolyte member and a pair of electrodes, the gas sensor outputting a detection signal corresponding to the concentration of a specific gas contained in exhaust gas, and which is applied to an internal combustion engine for which air-fuel-ratio feedback control is performed on the basis of the detection signal. The gas sensor apparatus comprises obtaining means for obtaining the detection signal output from the gas sensor; resistance detection means for detecting the internal resistance of the cell of the gas sensor; determination means for determining whether or not the value of the detection signal obtained by the obtaining means has reached a start determination value at which the air-fuel-ratio feedback control can be started; start-time resistance detection means, operable when the determination means determines that the value of the detection signal has reached the start determination value, for detecting the internal resistance of the cell, as a start-time internal resistance, through use of the resistance detection means; and comparison means for comparing the start-time internal resistance detected by the tart-time resistance detection means with a deterioration determination value set in advance.

Even before the gas sensor is heated to a target temperature and enters a completely activated state, in a period in which the internal resistance of the gas sensor decreases as a result of heating, the gas sensor becomes possible to output a detection signal whose level is sufficient for execution of air-fuel-ratio feedback control for an internal combustion engine. The present inventors found through studies that a correlation exists between the degree of deterioration of the cell and the internal resistance of the cell at the time when the value of the detection signal has reached the start determination value at which the air-fuel-ratio feedback control can be started. In view of this, in the first mode, the comparison between the start-time internal resistance of the cell and the deterioration determination value is performed when the value of the detection signal from the gas sensor reaches the start determination value for determining whether or not the detection signal has a degree of accuracy necessary for performing the air-fuel-ratio feedback control. With this configuration, the deterioration determination for the cell can be started at an earlier timing as compared with the case of a conventional gas sensor apparatus which performs the deterioration determination for the cell after the detection signal from the gas sensor becomes stable to a degree sufficient for performing the air-fuel-ratio feedback control. Also, since the deterioration determination for the cell can be performed through direct and simple comparison processing of comparing the start-time internal resistance of the cell with the deterioration determination value, the deterioration determination can be performed accurately and quickly. Also, deterioration correction processing or the like based on the result of the determination can be performed at an early timing.

In the first mode, the gas sensor may further comprise a heater for heating the solid electrolyte member when energization means supplies electricity to the heater. In this case, the gas sensor apparatus of the first mode may further comprise determination means for determining the amount of electricity supplied to the heater by the energization means such that the internal resistance detected by the resistance detection means coincides with a target resistance, and correction means for correcting the target resistance on the basis of the result of the comparison performed by the comparison means.

In the first mode, when the amount of electricity supplied to the heater is determined such that the internal resistance coincides with the target resistance, the target resistance can be corrected on the basis of the result of the comparison performed by the comparison means. Therefore, the amount of electricity supplied to the heater can be determined accurately. Thus, the cell, which is heated by the heater, is maintained at a constant temperature, whereby a more stable output can be obtained from the gas sensor.

According to a second mode of the present invention, there is provided a method of controlling a gas sensor apparatus which includes a gas sensor having at least one cell composed of a solid electrolyte member and a pair of electrodes, the gas sensor outputting a detection signal corresponding to the concentration of a specific gas contained in exhaust gas, and resistance detection means for detecting the internal resistance of the cell, and which is applied to an internal combustion engine for which air-fuel-ratio feedback control is performed on the basis of the detection signal. The method comprises an obtaining step of obtaining the detection signal output from the gas sensor; a determination step for determining whether or not the value of the detection signal obtained in the obtaining step has reached a start determination value at which the air-fuel-ratio feedback control can be started; a start-time resistance detection step, performed when the value of the detection signal is determined in the determination step to have reached the start determination value, for detecting the internal resistance of the cell, as a start-time internal resistance, through use of the resistance detection means; and a comparison step of comparing the start-time internal resistance detected in the tart-time resistance detection step with a deterioration determination value set in advance.

In the second mode, the comparison between the start-time internal resistance of the cell and the deterioration determination value is performed when the value of the detection signal from the gas sensor reaches the start determination value for determining whether or not the detection signal has a degree of accuracy necessary for performing the air-fuel-ratio feedback control. With this configuration, the deterioration determination for the cell can be started at an earlier timing as compared with the case of a conventional gas sensor apparatus which performs the deterioration determination for the cell after the detection signal from the gas sensor becomes stable to a degree sufficient for performing the air-fuel-ratio feedback control. Also, since the deterioration determination for the cell can be performed through direct and simple comparison processing of comparing the start-time internal resistance of the cell with the deterioration determination value, the deterioration determination can be performed accurately and quickly. Also, deterioration correction processing or the like based on the result of the determination can be performed at an early timing.

In the second mode, the gas sensor may further comprise a heater for heating the solid electrolyte member when energization means supplies electricity to the heater. In this case, the method of the second mode may further comprise a determination step of determining the amount of electricity supplied to the heater by the energization means such that the internal resistance detected by the resistance detection means coincides with a target resistance, and a correction step of correcting the target resistance on the basis of the result of the comparison performed in the comparison step.

In the second mode, when the amount of electricity supplied to the heater is determined such that the internal resistance coincides with the target resistance, the target resistance can be corrected on the basis of the result of the comparison performed by the comparison means. Therefore, the amount of electricity supplied to the heater can be determined accurately. Thus, the cell, which is heated by the heater, is maintained at a constant temperature, whereby a more stable output can be obtained from the gas sensor.

MODE FOR CARRYING OUT THE INVENTION

One embodiment of a gas sensor apparatus according to the present invention will now be described with reference to the drawings. First, the electrical configuration of an example gas sensor apparatus 1 will be described with reference to FIG. 1.

Figure 1:
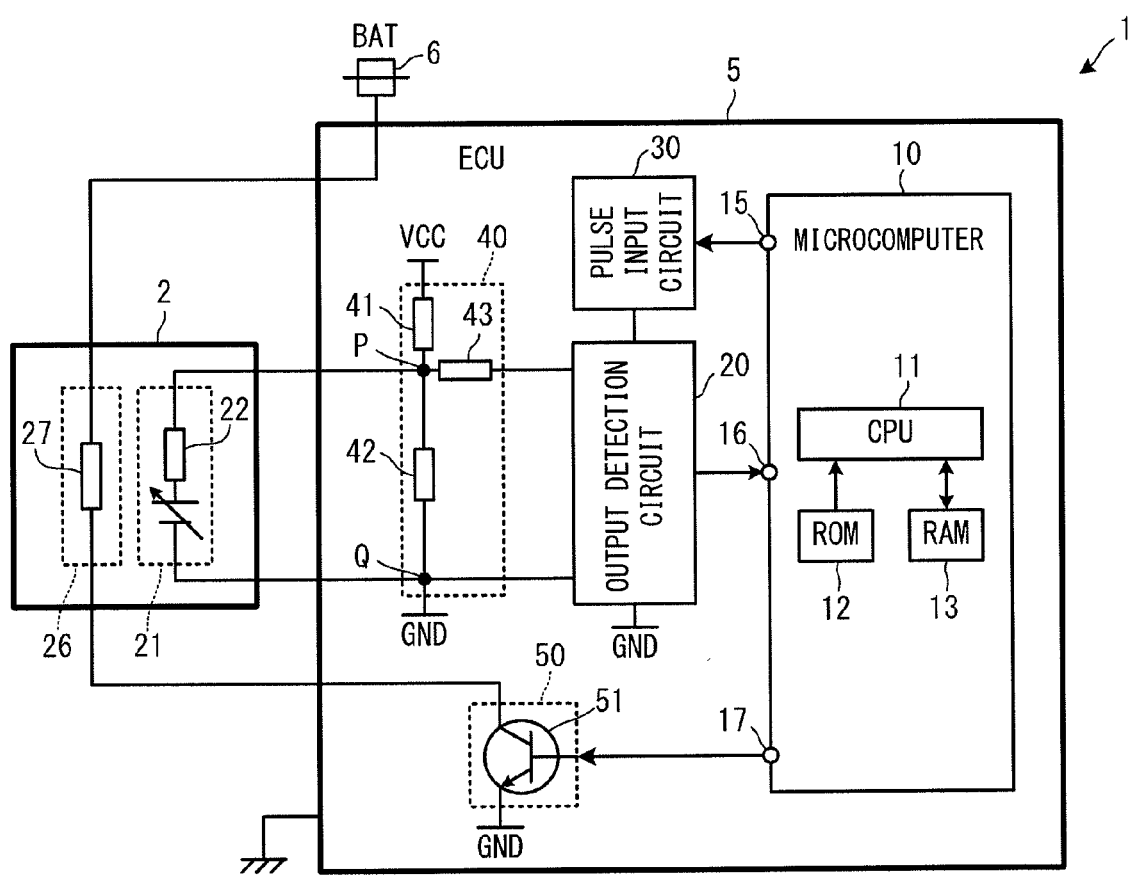
FIG. 1 Block diagram showing the electrical configuration of a gas sensor apparatus 1.

The gas sensor apparatus 1 shown in FIG. 1 is mounted on an automobile, and includes a gas sensor 2 and an electronic control unit (ECU) 5. The gas sensor 2 in the present embodiment is a λ-type oxygen sensor whose output value (value of a detection signal output therefrom) changes in accordance with the concentration of oxygen contained in exhaust gas discharged from an engine and changes sharply at a concentration corresponding to the stoichiometric air-fuel ratio. Since a publicly known oxygen sensor is used here, the details of its structure, etc. will not be provided. However, there will be briefly described the principle of operation of a sensor element used in the oxygen sensor so as to detect the air-fuel ratio of exhaust gas (the concentration of oxygen contained in exhaust gas).

A cell which constitutes the sensor element is composed of a solid electrolyte member formed of zirconia which exhibits oxygen-ion conductivity at its activation temperature or higher, and two porous electrodes formed of platinum and sandwiching the solid electrolyte member. The cell is formed into a tubular shape or a platelike shape. The cell detects the concentration of oxygen through utilization of a phenomenon that, when a difference in oxygen partial pressure arises between two atmospheres separated by the solid electrolyte member, oxygen ions move through the solid electrolyte member. Specifically, an exhaust gas atmosphere and a reference gas atmosphere (atmosphere having an oxygen concentration serving as a reference) are separated by the solid electrolyte member. When the oxygen partial pressures within the two atmospheres are balanced, electrons are carried by oxygen ions moving through the solid electrolyte member. As a result, an electromotive force (detection signal) is produced between the porous electrodes. This electromotive force greatly changes depending on whether or not excess oxygen remains after an unburned gas contained in the exhaust gas is burned completely through the catalytic action of the porous electrodes. Essentially, the electromotive force varies between two values corresponding to the cases where the air-fuel ratio is on the rich side and on the lean side; that is, sharply changes at a point where the air-fuel ratio of the exhaust gas coincides with the stoichiometric air-fuel ratio.

In general, when the air-fuel ratio of the exhaust gas is on the rich side in relation to the stoichiometric air-fuel ratio (the oxygen concentration of the exhaust gas is low and oxygen is insufficient for complete burning of unburned gas), the detection signal output from the sensor element has a potential difference of about 900 mV in relation to a reference potential. Meanwhile, when the air-fuel ratio of the exhaust gas is on the lean side in relation to the stoichiometric air-fuel ratio (the oxygen concentration of the exhaust gas is high and excess oxygen remains after complete burning of unburned gas), the detection signal output from the sensor element has a potential difference of about 50 mV in relation to the reference potential. The present embodiment will be described under the assumption that an oxygen sensor disclosed in Japanese Patent Application Laid-Open No. 2004-138599 is used as the oxygen sensor described above.

The gas sensor 2 shown in FIG. 1 has a structure in which a heater 26 is inserted into a sensor element which is formed into a bottomed tubular shape through use of a single cell 21, and the sensor element is held inside a metallic shell which is attached to an exhaust pipe (not shown). The heater 26, which is formed into a barlike or platelike shape, includes a heating resistor 27, which is mainly formed of platinum, tungsten, or the like and which is buried in a base member formed of insulating ceramic of alumina. When the gas sensor 2 is attached to the exhaust pipe, a distal end portion of the bottomed-tubular sensor element (located on the side toward the bottom of the tube) is inserted into the exhaust pipe so that one porous electrode of the cell 21 (the electrode formed on the outer circumference of the sensor element) is exposed to exhaust gas. The other porous electrode of the cell 21 (the electrode formed on the inner circumference of the sensor element) is exposed to a reference gas (air in the present embodiment) introduced into the tube from the outside of the exhaust pipe. Thus, as described above, the air-fuel ratio of the exhaust gas (the oxygen concentration of the exhaust gas) is detected.

The cell 21 has an internal resister 22. It has been known that the resistance (internal resistance, impedance) of the internal resistor 22 decreases as the temperature of the solid electrolyte member increases, and has a predetermined correlation with the temperature of the cell 21. In the gas sensor apparatus 1, the internal resistance of the cell 21 is detected, and the electric power supplied to the heater 26 is controlled such that the internal resistance coincides with a target resistance. Thus, the temperature of the cell 21 is stabilized such that the cell 21 is maintained at a target temperature.

The ECU 5 is an apparatus for performing control of the unillustrated engine, including air-fuel-ratio feedback control (e.g., adjustment of the amount of fuel injected from an injector), on the basis of the detection signal output from the gas sensor 2. In the present embodiment, the ECU 5 detects the internal resistance of the cell 21 on the basis of the detection signal output from the gas sensor 2, determines the degree of deterioration of the cell 21, corrects the target resistance, and accurately controls the heater 26 through PID control. The configuration necessary for such operation will be described. The ECU 5 includes a microcomputer 10, an output detection circuit 20, a pulse input circuit 30, an offset circuit 40, and a heater control circuit 50. The microcomputer 10 includes a CPU 11 which governs the control of the ECU 5; ROM 12 which stores a deterioration correction program to be described later, etc.; RAM 13 which temporarily stores various data; and input and output ports 15, 16, and 17 for receiving and outputting signals. Notably, the CPU 11, ROM 12, and RAM 13 of the microcomputer 10 have known configurations.

The output detection circuit 20, which is a known circuit including resistors, etc., is electrically connected to opposite ends of the cell 21 of the gas sensor 2; that is, the two porous electrodes, via the offset circuit 40. The detection signal output from the cell 21 is inputted to the output detection circuit 20, whereby a potential difference between the opposite ends of the cell 21 is detected. The electromotive force generated in the cell 21 can be detected from the potential difference between the opposite ends of the cell 21. The output detection circuit 20 obtains (detects) the potential difference between the opposite ends of the cell 21 at predetermined intervals, and outputs it to the A/D port 16 of the microcomputer 10 as a signal representing the electromotive force of the cell 21.

Also, the output detection circuit 20 has an unillustrated sample hold circuit, and can hold the obtained potential difference between the opposite ends of the cell 21. As will be described in detail later, when a pulse voltage is applied to the cell 21, the potential difference between the opposite ends changes in accordance with the internal resistance of the cell 21. Therefore, when the internal resistance of the cell 21 is to be detected, a pulse voltage is applied to the cell 21 by the pulse input circuit 30. The output detection circuit 20 also detects the potential difference between the opposite ends when the pulse voltage is applied to the cell 21. At that time, the potential difference between the opposite ends of the cell 21 immediately before the application of the pulse voltage is held in the sample hold circuit. The output detection circuit 20 outputs to the A/D port 16 of the microcomputer 10 the difference between the potential difference in the case where the pulse voltage is not applied and that in the case where the pulse voltage is applied; that is, a change in the potential difference caused by the application of the pulse voltage, as a signal representing the internal resistance of the cell 21.

The offset circuit 40 is provided in wiring lines which connect the opposite ends of the cell 21 to the output detection circuit 20, and offsets the potential of the electromotive force output from the cell 21. Specifically, a resistor 42 is connected to a node P on a wiring line which establishes connection between the higher-potential side end of the cell 21 and the output detection circuit 20 and to a node Q on a wiring line which establishes connection between the lower-potential side end of the cell 21 and the output detection circuit 20. The node Q on the lower potential side is connected to a reference potential line (GND) of the ECU 5. Notably, the reference potential line of the ECU 5 is connected to, for example, the body of the automobile. The node P on the higher potential side is connected, via a resistor 41, to a power supply which outputs a predetermined power supply voltage VCC. Also, a resistor 43 for noise prevention is connected between the node P and the output detection circuit 20.

As described above, the solid electrolyte member, which partially constitutes the cell 21 has a characteristic such that its internal resistance (impedance) decreases as the temperature of the solid electrolyte member increases. That is, in a state in which the temperature of the solid electrolyte member is low (hereinafter may be referred to a "non-active state"), the internal resistance is high, and the cell 21 substantially becomes insulative. Also, as the temperature increase of the solid electrolyte member increases, the internal resistance decreases, and the cell 21 is activated. In a state in which the cell 21 is activated (hereinafter may be referred to as an "active state"), the internal resistance is low. When the air-fuel ratio of the exhaust gas is on the rich side, the electromotive force of the cell 21 has a potential difference of about 900 mV in relation to the reference potential. When the air-fuel ratio of the exhaust gas is on the lean side, the electromotive force of the cell 21 has a potential difference of about 50 mV in relation to the reference potential.

The power supply voltage VCC is divided by the resistor 41 and the resistor 42 such that the potential at the node P becomes about 450 mV. The resistor 42 is selected such that its resistance is sufficiently smaller than the internal resistance of the cell 21 in the non-active state, and is sufficiently lager than the internal resistance of the cell 21 in the active state. When the cell 21 is in the non-active state, no current flows through the cell 21, and no electromotive force is generated. Therefore, the output of the cell 21 is 0 V. However, the output detection circuit 20 receives about 450 mV from the offset circuit 40 as the output of the cell 21. Meanwhile, when the cell 21 is in the active state, current hardly flows through the resistor 42 whose resistance is sufficiently larger than the internal resistance. Therefore, the voltage which the output detection circuit 20 receives from the offset circuit 40 as the output value of the cell 21 (the value indicated by the detection signal) is substantially equal to the electromotive force of the cell 21.

The heater control circuit 50 includes a transistor 51, for example. The collector of the transistor 51 is connected to one end of the heater 26, the emitter of the transistor 51 is connected to the reference potential line via a predetermined resistor (not shown), and the base of the transistor 51 is connected to the PWM port 17 of the microcomputer 10. The other end of the heater 26 is connected to a battery 6, which supplies electric power to the ECU 5. The energization of the heater 26 is controlled by the microcomputer 10 through PID control. Electricity is supplied from the heater control circuit 50 to the heater 26 through PWM control performed on the basis of a duty ratio computed by the microcomputer 10. Specifically, a signal for turning the transistor 51 on and off is output from the PWM port 17 of the microcomputer 10 so as to control the current flowing between the collector and emitter of the transistor 51; that is, the current flowing from the battery 6 to the heater 26. Notably, the heater control circuit 50 may be configured through use of an FET or the like instead of the transistor 51.

The pulse input circuit 30 is a circuit for applying a pulse voltage having a rectangular waveform to the cell 21 via the output detection circuit 20. Digital data representing a rectangular pulse waveform are generated through computation performed by the microcomputer 10, and are output from the I/O port 15 to the pulse input circuit 30. The pulse input circuit 30 generates a rectangular pulse voltage on the basis of the received pulse waveform data, and applies the pulse voltage to the cell 21. Notably, the application time of the pulse voltage can be properly determined within a range of several ms to several hundreds of ms.

As described above, as a result of application of the pulse voltage to the cell 21, the potential difference between the opposite ends of the cell 21, which is acquired (detected) by the output detection circuit 20, changes temporarily. In other words, the potential generated between the opposite ends of the cell 21 as a result of application of the pulse voltage is added to the electromotive force of the cell 21, and the sum of the potential and the electromotive force is acquired (detected) by the output detection circuit 20 as the detection signal output from the cell 21. Therefore, the internal resistance of the cell 21 (thus, the temperature of the cell 21, which has a correlation with the internal resistance) can be computed from the change in the potential difference between the opposite ends of the cell 21, which change is produced as a result of application of the pulse voltage and is obtained by the output detection circuit 20 as a detection signal. In the gas sensor apparatus 1, when the cell 21 is in the active state, electric power is supplied to the heater 26 through PWM control based on PID control, as described above, such that the internal resistance of the cell 21 coincides with the target resistance.

In the gas sensor apparatus 1 having the above-described configuration, the output (about 900 mV when the air-fuel ratio of the exhaust gas is on the rich side, and about 50 mV when the air-fuel ratio of the exhaust gas is on the lean side) is obtained when the cell 21 is heated to at least a predetermined temperature (hereinafter referred to as a "high-temperature control temperature") which is sufficiently higher than the activation temperature. The high-temperature control temperature is set to 700° C., for example. In the case where the temperature of the cell 21 is equal to or higher than the activation temperature and lower than the high-temperature control temperature, although an output (detection signal) can be obtained from the cell 21, only a small difference is produced between the value of the detection signal obtained when the air-fuel ratio of the exhaust gas is on the rich side and the value of the detection signal obtained when the air-fuel ratio of the exhaust gas is on the lean side.

Immediately after the engine is started, the temperature of the engine is still low, and the exhaust gas may contain water droplets. If such a water droplet adheres to the cell 21 whose temperature has increased to a high temperature as a result of heating by the heater 26, the water droplet evaporates at the surface of the cell 21, and locally removes heat from the cell 21. As a result, a heat shock is applied to the cell 21, and the cell 21 may break (for example, may crack). Therefore, in the gas sensor apparatus 1, during a period after the startup of the engine in which the exhaust gas may contain water droplets (hereinafter referred to as the "water presence period"), the heating temperature of the cell 21 is maintained at a low temperature (hereinafter referred to as a "water-presence-period control temperature"), at which temperature the cell 21 can be activated, but the cell 21 does not crack even when a water droplet adheres to the cell 21. Notably, the water-presence-period control temperature, which is equal to or higher than the activation temperature but lower than the high-temperature control temperature, is set to 400° C., for example. The water presence period changes depending on the design of the engine, and is set in advance for each engine for which the gas sensor apparatus 1 is used.

The gas sensor apparatus 1 determines whether or not the cell 21 of the gas sensor 2 has deteriorated. In the case where the cell 21 has deteriorated due to, for example, elapse of time, the internal resistance of the cell 21 at a certain temperature becomes higher than that when the cell 21 has not yet deteriorated. As described above, the internal resistance decreases as the temperature of the solid electrolyte member increases. Therefore, in the case where the cell 21 has deteriorated, if the heater 26 is controlled such that the internal resistance coincides with the target resistance, the temperature of the cell 21 may increase excessively. In order to solve such a problem, in the present embodiment, the CPU 11 of the microcomputer 10 executes a deterioration correction program when operation of the gas sensor apparatus 1 is started, and performs the deterioration determination for the cell 21 in accordance with the program and on the basis of the internal resistance first obtained after the output of the cell 21 satisfies a predetermined condition (hereinafter referred to as a "start-time internal resistance").

Figure 2A:
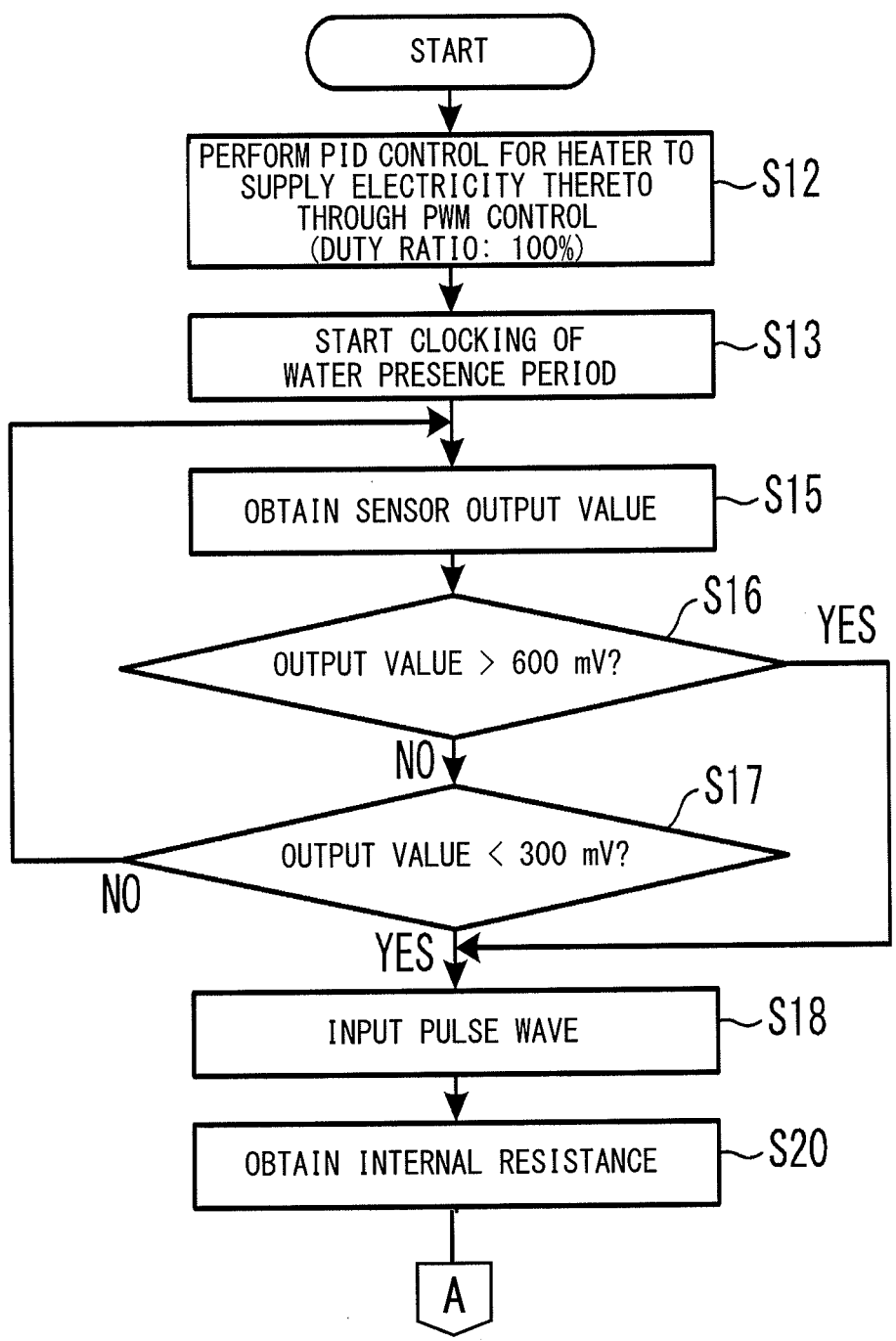
FIGS. 2A and 2B Flowcharts showing a deterioration correction program.
Figure 2B:
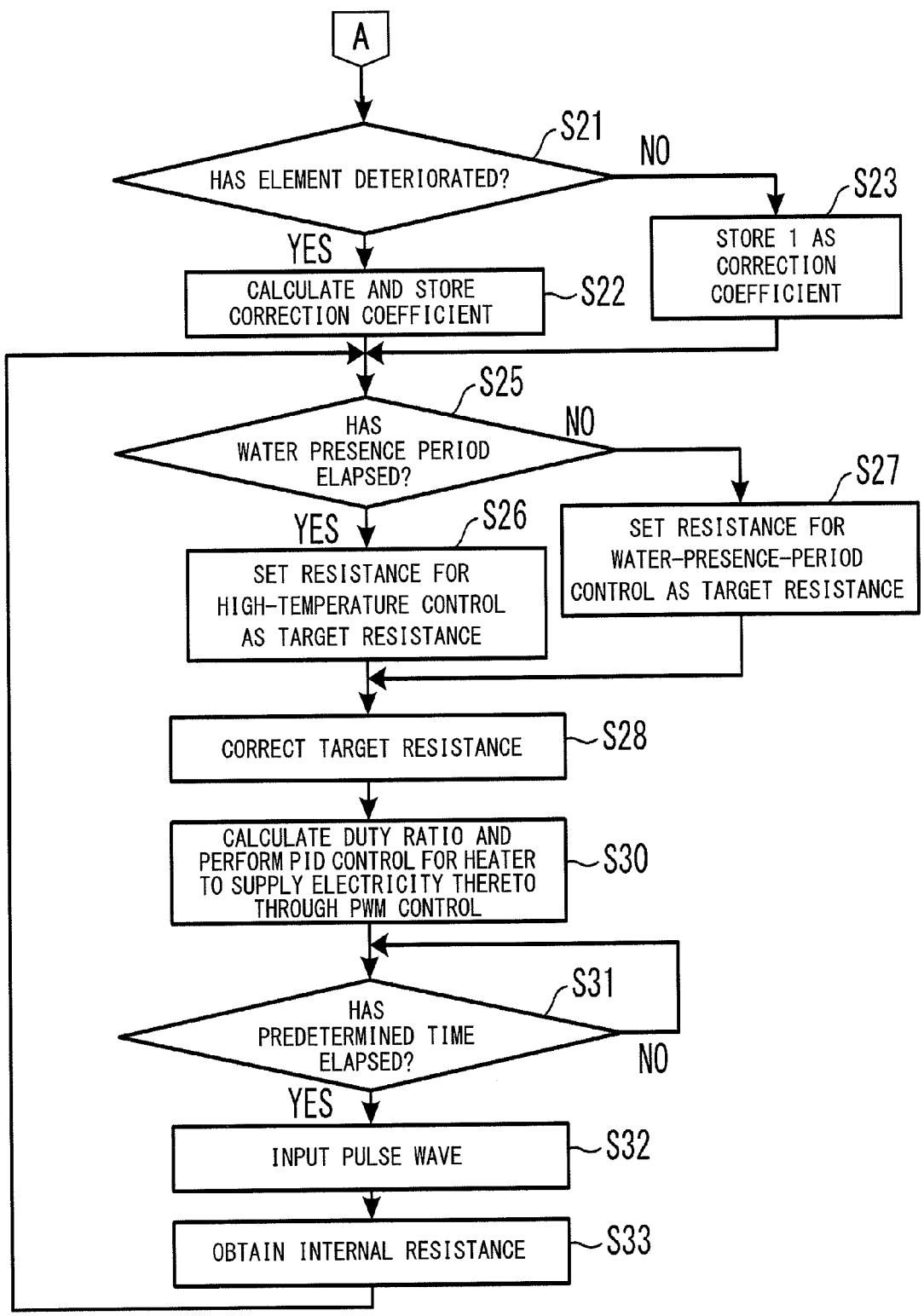

In the case where the cell 21 has deteriorated, the microcomputer 10 changes (corrects) the target resistance in accordance with the deterioration correction program. As a result, in the gas sensor apparatus 1, the energization control (PID control) is performed for the heater 26 in accordance with the degree of deterioration of the cell 21. Therefore, the temperature of the cell 21 can be maintained constant irrespective of the degree of deterioration of the cell 21. Hereinafter, the processing which is performed by the microcomputer 10 in accordance with the deterioration correction program, which is shown in FIGS. 2A and 2B in the form of a flowchart, will be described with reference to FIGS. 1 and 3 when necessary.

First, there will be described tables (a deterioration table and a correction coefficient table) and variables (a resistance for water-presence-period control and a resistance for high-temperature control) which are referred to in the deterioration correction program. The deterioration table is a table which shows a value of the internal resistance which the cell 21 can assume before deteriorating (hereinafter referred to as a "deterioration determination value"). This table is prepared in advance and is stored in the ROM 12. The correction coefficient table is a table which shows an experimentally obtained relation between the start-time internal resistance of the cell 21 and the value of the correction coefficient, which increases with the start-time internal resistance. This table is also prepared in advance and is stored in the ROM 12. In the present embodiment, when the value of the detection signal output from the gas sensor 2 reaches a level (accuracy) required for starting the air-fuel-ratio feedback control, the start-time internal resistance of the cell 21 is obtained, and is compared with the deterioration determination value. Before performing air-fuel-ratio feedback control on the basis of the output value of the cell 21 (the value of the detection signal), the ECU 5 performs air-fuel-ratio open loop control (control of changing the air-fuel ratio to the rich and lean sides in a predetermined pattern by changing the amount of fuel injected from the injector in a predetermined pattern). More specifically, in the present embodiment, when the output value of the cell 21 (the value of the detection signal) represents a voltage higher than 600 mV or a voltage lower than 300 mV, the value of the detection signal is determined to have a degree of accuracy necessary for starting the air-fuel-ratio feedback control (closed loop control of the air-fuel ratio), and the start-time internal resistance is obtained. Notably, 600 mV and 300 mV, which are upper and lower limit values compared with the output value), are mere examples, and may be properly determined in accordance with the output value of the cell 21.

In the case where the output value of the cell 21 (the value of the detection signal) has reached a start determination value and the deterioration determination is performed, the deterioration determination value obtained with reference to the deterioration table is compared with the start-time internal resistance obtained from the cell 21 so as to determine whether or not the cell 21 has deteriorated. Notably, the voltage values (specifically, 600 mV and 300 mV), which are compared with the output value so as to determine whether or not the output value has a degree of accuracy necessary for performing the air-fuel-ratio feedback control, correspond to the "start determination value" in the present invention.

The ROM 12 stores target resistances which are used for the temperature control performed for the heater 26 such that the internal resistance becomes equal to one of the target resistances. As described above, the temperature of the heater 26 is controlled to the water-presence-period control temperature before elapse of the water presence period, and is controlled to the high-temperature control temperature after elapse of the water presence period. Notably, the target resistances stored in the ROM 12 include an internal resistance corresponding to the water-presence-period control temperature (hereinafter referred to as the "resistance for water-presence-period control") and an internal resistance corresponding to the high-temperature control temperature (hereinafter referred to as the "resistance for high-temperature control") for the case where the cell 21 has not yet deteriorated.

Next, there will be described operation of the gas sensor apparatus 1 when the deterioration correction program is executed. Notably, in the following description, each step in the flowchart is abbreviated to "S."

Figure 3:
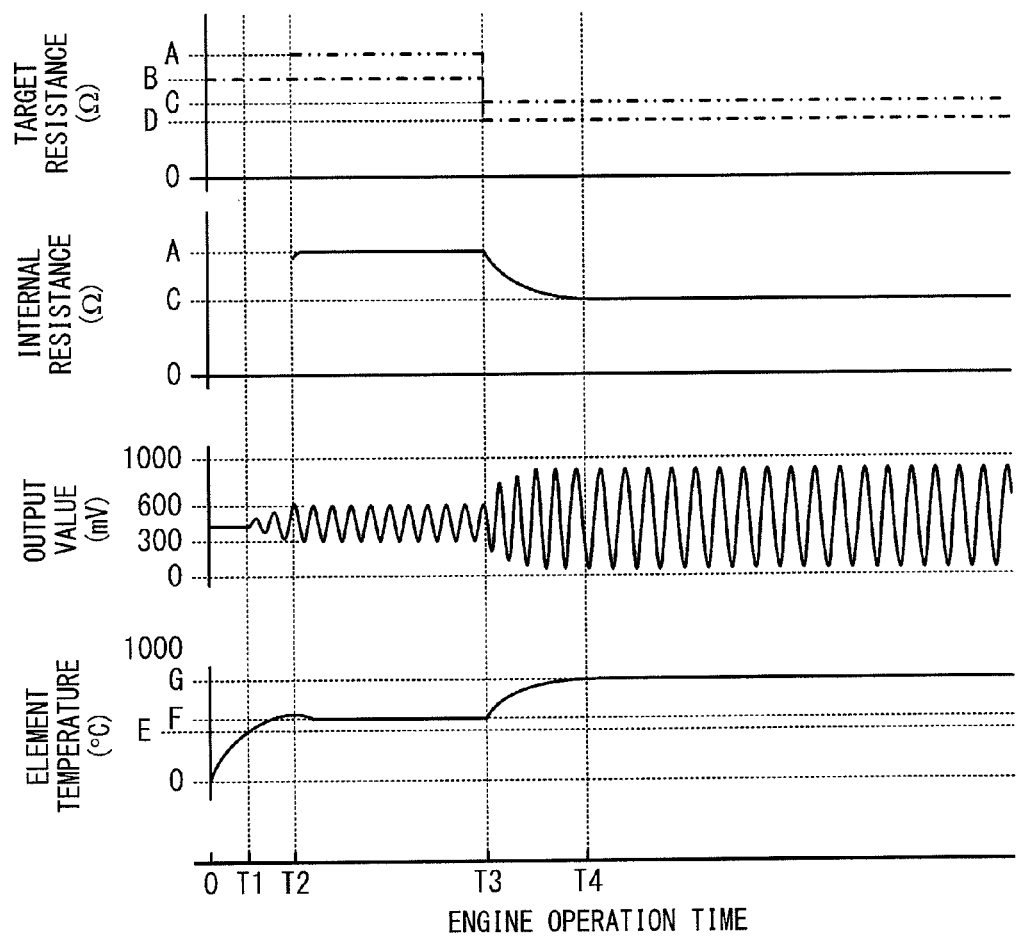
FIG. 3 Graph showing the relation between the time elapsed after startup of an engine and the output value of a cell 21, element temperature, etc.

The gas sensor apparatus 1 is powered, for example, when the engine of the automobile is started, and the CPU 11 of the microcomputer 10 starts the execution of the deterioration correction program stored in the ROM 12. As shown in FIG. 2A, the CPU 11, which has started the deterioration correction program, sets the duty ratio used in the PWM control to a fixed value (S12). Notably, in the present embodiment, this duty ratio is set to 1 (100%), and a continuous ON/OFF signal is output to the heater control circuit 50 (in this case, an normally ON signal is output to the heater control circuit 50). Specifically, in a heater control program (not shown) which is executed in parallel with the deterioration correction program, a PWM control signal for tuning the transistor 51 on and off in accordance with the duty ratio is generated, and is output to the heater control circuit 50. The voltage of the battery 6 is applied to the heating resistor 27 of the heater 26 as it is, whereby the temperature of the cell 21 increases with time as shown in FIG. 3.

Next, as shown in FIGS. 2A and 2B, the CPU 11 starts the clocking of the water presence period (S13). As described above, the water presence period has a time length set in accordance with the engine for which the gas sensor apparatus 1 is used, and is stored in the ROM 12.

The CPU 11 obtains the output (detection signal) of the gas sensor 2 (S15). The detection signal of the cell 21 obtained via the output detection circuit 20 is input to the microcomputer 10 via the A/D port 16, and the CPU 11 reads the value of the detection signal. Since the detection signal is offset as described above, the detection signal from the cell 21 in the non-active state represents a voltage of about 450 mV in the period of 0 to T1 shown in FIG. 3. At time T1, before which the internal resistance of the cell 21 has decreased to some degree as a result of the increased temperature of the cell 21, the electromotive force generated at the cell 21 starts to change with a change in the air-fuel ratio (specifically, the air-fuel ratio during the period in which open loop control is executed). That is, when the air-fuel ratio changes to the rich side, the voltage of the detection signal from the cell 21 becomes higher than 450 mV, and, when the air-fuel ratio changes to the lean side, the voltage of the detection signal from the cell 21 becomes lower than 450 mV. Moreover, the difference between the value of the detection signal when the air-fuel ratio of the exhaust gas is on the rich side and the value of the detection signal when the air-fuel ratio of the exhaust gas is on the lean side increases as the temperature of the cell 21 increases.

As shown in FIGS. 2A and 2B, as long as the value (voltage) of the detection signal is not higher than 600 mV (S16: NO) and is not lower than 300 mV (S17: NO), the CPU 11 returns to S15 so as to repeat the monitoring of the value of the detection signal. In a state in which the temperature of the cell 21 is lower than the activation temperature (indicated by a solid line E in FIG. 3) (in the period of 0 to T1 (see FIG. 3)), the voltage of the detection signal is about 450 mV. Even after the temperature of the cell 21 has reached the activation temperature, the voltage of the detection signal becomes 600 mV or lower when the air-fuel ratio is on the rich side and becomes 300 mV or higher when the air-fuel ratio is on the lean side, in a period in which the cell 21 has not yet been heated sufficiently (in the period of T1 to T2 (see FIG. 3)). In such a case, despite that the cell 21 is activated, the difference between the value of the detection signal when the air-fuel ratio of the exhaust gas is on the rich side and the value of the detection signal when the air-fuel ratio of the exhaust gas is on the lean side is small, and the accuracy required for detecting the air-fuel ratio of the exhaust gas cannot be obtained satisfactorily.

In the case where the output (output voltage) of the cell 21 becomes higher than 600 mV when the air-fuel ratio of the exhaust gas changes to the rich side (S16: YES) or in the case where the output (output voltage) of the cell 21 becomes lower than 300 mV when the air-fuel ratio of the exhaust gas changes to the rich side (S17: YES), the CPU 11 proceeds to S18. The graph of FIG. 3 shows an example case where the output of the cell 21 becomes greater than 600 mV at T2. Since the engine has already been started, the air-fuel ratio of the exhaust gas changes momentarily. If the output value of the cell 21 becomes greater than 600 mV or smaller than 300 mV, the cell 21 is determined to have been activated to a degree required for obtaining a necessary accuracy for detection of the air-fuel ratio of the exhaust gas. As a result, the ECU 5 can change the separately performed air-fuel-ratio open loop control to the known air-fuel-ratio feedback control (closed loop control of the air-fuel ratio) performed on the basis of the output (detection signal) of the cell 21.

The CPU 11 outputs digital data representing a pulse waveform to the pulse input circuit 30 via the I/O port 15 (S18). The pulse input circuit 30 generates a rectangular pulse voltage, and applies the pulse voltage to the cell 21. The output detection circuit 20 obtains the potential of the cell 21 having changed as a result of application of the pulse voltage, and outputs it to the A/D port 16 of the microcomputer 10. The CPU 11 computes the internal resistance of the cell 21 from the obtained potential of the cell 21 having changed as a result of application of the pulse voltage (S20). Notably, the internal resistance of the cell 21 obtained in S20 is the start-time internal resistance.

A deterioration determination value (previously set deterioration determination value) is obtained (set) with reference to the deterioration table stored in the ROM 12. The start-time internal resistance of the cell 21 obtained in S20 is compared with the deterioration determination value. In the case where the start-time internal resistance coincides with the deterioration determination value or the difference therebetween is equal to or less than a predetermined value, the cell 21 is determined not to have deteriorated (S21: NO). In this case, the correction coefficient for correcting the target resistance, which will be described later, is set to 1, and is stored in the RAM 13.

Meanwhile, in the case where the difference between the start-time internal resistance of the cell 21 and the deterioration determination value is greater than the predetermined value, the cell 21 is determined to have deteriorated (S21: YES). In this case, a value of the correction coefficient corresponding to the start-time internal resistance is calculated (determined) with reference to the above-mentioned correction coefficient table which shows the relation between the start-time internal resistance and the correction coefficient, and is stored in the RAM 13 (S22). Notably, the method of calculating the correction coefficient is not limited to that using the correction coefficient table, and the correction coefficient may be calculated through use of an arithmetic expression (function) which is empirically obtained for calculation of the correction coefficient necessary for increasing the target resistance with the difference between the start-time internal resistance and the deterioration determination value.

Next, the CPU 11 determines whether or not the water presence period whose clocking has been started in S13 has elapsed (S25). In the case where the water presence period has not yet elapsed (the period of T2 to T3 (see FIG. 3)), in order to prevent the cell 21 from breaking, such as cracking, due to adhesion of water thereto, the heating temperature of the cell 21 is maintained at the water-presence-period control temperature (indicated by a solid line F in FIG. 3). As described above, the temperature control for the heater 26 is performed through PID control such that the internal resistance of the cell 21 coincides with the target resistance. The supply of electricity to the heater 26 is performed though PWM control, and the duty ratio therefor is obtained, through known PID computation, from the internal resistance and the target resistance.

Before the water presence period elapses (S25: NO), the resistance for water-presence-period control (indicated by an alternate long and short dash line B in FIG. 3) is read out of the ROM 12, and is set to a memory area for the target resistance (S27). Then, the correction coefficient stored in S22 or S23 is read out, and is applied to the target resistance set in S27, whereby the target resistance is corrected in accordance with the degree of deterioration of the cell 21 (S28). In the case where the cell 21 has not yet deteriorated, since 1 is set to a memory area for the correction coefficient, the target resistance before being subjected to the correction in S28 and the target resistance after being subjected to the correction in S28 have the same value, and the target resistance indicated by the alternate long and short dash line B in FIG. 3 is maintained. Meanwhile, in the case where the cell 21 has deteriorated, in S28, the target resistance is corrected through use of the correction coefficient stored in S22 such that the target resistance increases as indicated by an alternate long and two short dashes line A in FIG. 3.

The CPU 11 performs PID computation on the basis of the internal resistance of the cell 21 obtained in S20 and the target resistance corrected in S28, and calculates the duty ratio used for controlling the supply of electricity to the heater 26 through PWM control. Then, the CPU 11 continuously outputs an ON/OFF signal to the heater control circuit 50 (S30). That is, by means of the heater control program (not shown), a PMW control signal for turning the transistor 51 on and off in accordance with the duty ratio is generated, and is output to the heater control circuit 50. The voltage of the battery 6 having undergone PWM control is applied to the heating resistor 27 of the heater 26. As shown in the period of T2 to T3 of FIG. 3, electricity is supplied to the heater 26 such that the internal resistance of the cell 21 coincides with the target resistance obtained by correcting the resistance for water-presence-period control through use of the correction coefficient stored in S22 or S23, whereby the temperature of the cell 21 is maintained at the water-presence-period control temperature (solid line F).

Next, as shown in FIGS. 2A and 2B, the CPU 11 waits for elapse of a predetermined time (e.g., 10 to 50 msec) (S31: NO). When the CPU 11 determines that the predetermined time has elapsed (S31: YES), the CPU 11 applies the pulse voltage to the cell 21 as in the case of S18 (S32). Then, the CPU 11 obtains the internal resistance of the cell 21, as in the case of S20 (S33), and returns to S25. As described above, S27 and S28 to S33 are repeated until the water presence period elapses (S25: NO). As a result, the temperature of the cell 21 is maintained at the water-presence-period control temperature.

When the CPU 11 detects at T3 (see FIG. 3) that the water presence period has elapsed (S25: YES), the CPU 11 performs a control for maintaining the heating temperature of the cell 21 at the high-temperature control temperature (indicated by a solid line G in FIG. 3) in order to enhance the detection accuracy of the air-fuel ratio (the detection accuracy of the oxygen concentration). The resistance for high-temperature control (indicated by an alternate long and short dash line D in FIG. 3) is read out of the ROM 12, and is set to the memory area for the target resistance (S26). As in the above-described case, the correction coefficient stored in S22 or S23 is read out, and is applied to the target resistance, whereby the target resistance is corrected in accordance with the degree of deterioration of the cell 21 (S28). Notably, in the case where the cell 21 has not yet deteriorated, since 1 is set to the memory area for the correction coefficient, the target resistance before being subjected to the correction in S28 and the target resistance after being subjected to the correction in S28 have the same value, and the target resistance indicated by the alternate long and short dash line D in FIG. 3 is maintained. Meanwhile, in the case where the cell 21 has deteriorated, in S28, the target resistance is corrected through use of the correction coefficient stored in S22 such that the target resistance increases as indicated by an alternate long and two short dashes line C in FIG. 3.

After that, in the same manner as described above, electricity is supplied to the heater 26 through PWM control performed in accordance with the duty ratio obtained through PID computation based on the internal resistance of the cell 21 obtained in S20 and the target resistance corrected in S28 (S30). As a result, electricity is supplied to the heater 26 such that the internal resistance of the cell 21 coincides with the target resistance obtained by correcting the resistance for high-temperature control through use of the correction coefficient stored in S22 or S23, whereby the temperature of the cell 21 is maintained at the high-temperature control temperature (solid line G).

Subsequently, the CPU 11 waits for elapse of the predetermined time (S31: NO). When the CPU 11 determines that the predetermined time has elapsed (S31: YES), through application of the pulse voltage to the cell 21 (S32), the CPU 11 obtains the internal resistance of the cell 21 (S33). Thereafter, the CPU 11 returns to S25. In this manner, after the water presence period (S25: YES), S26 and S28 to S33 are repeated. As a result, after time T3 shown in FIG. 3, electricity is supplied to the heater 26 such that the internal resistance of the cell 21 coincides with the target resistance obtained by correcting the resistance for high-temperature control in accordance with the degree of deterioration. After time T4, at which the CPU 11 determines that the temperature of the cell 21 has reached the high-temperature control temperature, the CPU 11 continues the PID control for the heater 26 such that the high-temperature control temperature is maintained. The output voltage (detection signal) of the cell 21 stably becomes about 900 mV when the air-fuel ratio of the exhaust gas changes to the rich side, and about 50 mV when the air-fuel ratio of the exhaust gas changes to the leans side. Thus, accurate detection of the air-fuel ratio of the exhaust gas becomes possible.

As described above, in the gas sensor apparatus 1, the comparison between the start-time internal resistance of the cell 21 and the deterioration determination value is performed when the output value of the detection signal reaches the start determination value for determining whether or not the detection signal has a degree of accuracy necessary for performing the air-fuel-ratio feedback control. As a result, the deterioration determination for the cell 21 can be started at an earlier timing as compared with the case of a conventional gas sensor apparatus which performs the deterioration determination for the cell after the detection signal becomes stable to a degree sufficient for performing the air-fuel-ratio feedback control. Also, since the deterioration determination for the cell 21 can be performed through direct and simple comparison processing of comparing the start-time internal resistance of the cell 21 with the deterioration determination value, the deterioration determination can be performed accurately and quickly. Also, deterioration correction processing or the like based on the result of the determination can be performed at an early timing.

Moreover, when the amount of electricity supplied to the heater 26; more specifically, the duty ratio used for supplying electricity to the heater 26 through PWM control, is determined such that the internal resistance coincides with the target resistance, the target resistance can be corrected through use of the correction coefficient obtained in accordance with the degree of deterioration of the cell 21. Therefore, the duty ratio can be obtained accurately. As a result, the cell 21, which is heated by the heater 26, is maintained at a constant temperature, whereby a more stable output can be obtained from the gas sensor 2.

Notably, the present invention is not limited to the above-described embodiment, and various modifications may be added thereto without departing from the scope of the present invention. In the embodiment, in S21 of the deterioration correction program, the CPU 11 determines whether or not the cell 21 has deteriorated through comparison between the start-time internal resistance of the cell 21 and the deterioration determination value. At that time, the CPU 11 may determine the degree of deterioration, while determining whether or not the cell 21 has deteriorated. For example, the CPU 11 may determine the transitional state of deterioration of the cell 21 from the potential which has changed as a result of application of the pulse voltage. In this case, a plurality of deterioration determination values may be provided for the comparison with the start-time internal resistance of the cell 21. This makes it possible to determine the degree of deterioration of the cell 21 in a plurality of levels, the number of which corresponds to the number of the deterioration determination values. Thus, it becomes possible to accurately correct the target resistance in accordance with the degree of deterioration of the cell 21 by determining the degree of deterioration of the cell 21 in the plurality of levels and calculating the correction coefficient, used for correction of the target resistance, in accordance with different calculation methods selectively used in consideration of the degree of deterioration.

Also, when the start-time internal resistance and the deterioration determination value are compared, the difference therebetween is compared with a predetermined value. In the above-described embodiment, this predetermined value is fixed irrespective of whether the air-fuel ratio is on the rich side or the lean side. However, the predetermined value may be changed depending on whether the air-fuel ratio is on the rich side or the lean side.

In the present embodiment, a pulse voltage is applied to the cell 21 in order to obtain the internal resistance of the cell 21. However, a pulse current or AC voltage may be applied to the cell 21 in order to obtain the internal resistance.

Also, a controller for controlling the operation of the gas sensor 2 may be disposed between the gas sensor 2 and the ECU 5 so as to constitute a gas sensor apparatus in cooperation with the gas sensor 2.

In the deterioration correction program of the present embodiment, the CPU 11 determines a period in which the cell 21 is maintained at the water-presence-period control temperature by starting the measurement of the water presence period in S13, and determining in S25 whether or not the water presence period has elapsed. However, the method of determining such a period is not limited thereto, and the period in which the cell 21 is maintained at the water-presence-period control temperature may be determined by determining whether or not the operating state of the internal combustion engine or information from a water temperature sensor or exhaust temperature sensor separately attached to the vehicle satisfies a predetermined condition. For example, the above-described deterioration correction program may be modified by removing S13 and modifying the processing of S25 such that the CPU 11 determines in S25 whether or not the water temperature measured on the basis of the output of the water temperature sensor is higher a predetermined temperature, and the CPU 11 proceeds to S26 when the water temperature is higher than the predetermined temperature and proceeds to S27 when the water temperature is equal to or lower than the predetermined temperature, The gas sensor apparatus 1 includes an oxygen censor whose sensor element is composed of a single cell. However, the present invention may be applied for one cell of a full-range air-fuel ratio composed of two cells or an NOx sensor composed of three cells.

DESCRIPTION OF REFERENCE NUMERALS

1: gas sensor apparatus
2: gas sensor
5: ECU
10: microcomputer
11: CPU
12: ROM
13: RAM
20: output detection circuit
21: cell
26: heater
30: pulse input circuit
50: heater control circuit

The invention claimed is:

1. A gas sensor apparatus which includes a gas sensor having at least one cell composed of a solid electrolyte member and a pair of electrodes, the gas sensor outputting a detection signal corresponding to the concentration of a specific gas contained in exhaust gas, and which is applied to an internal combustion engine for which air-fuel-ratio feedback control is performed on the basis of the detection signal, the gas sensor apparatus comprising:

obtaining means for obtaining the detection signal output from the gas sensor;
   resistance detection means for detecting the internal resistance of the cell of the gas sensor;
   determination means for determining whether or not the value of the detection signal obtained by the obtaining means has reached a start determination value at which the air-fuel-ratio feedback control can be started;
   start-time resistance detection means, operable when the determination means determines that the value of the detection signal has reached the start determination value, for detecting the internal resistance of the cell, as a start-time internal resistance, through use of the resistance detection means; and
   comparison means for comparing the start-time internal resistance detected by the start-time resistance detection means with a deterioration determination value set in advance,
   wherein the start determination value is a value reached by the detection signal prior to the gas sensor entering an activated state at which time the detection signal becomes stable.

2. A gas sensor apparatus according to claim 1, wherein
   the gas sensor further comprises a heater for heating the solid electrolyte member when energization means supplies electricity to the heater; and
   the gas sensor apparatus further comprises determination means for determining the amount of electricity supplied to the heater by the energization means such that the internal resistance detected by the resistance detection means coincides with a target resistance, and correction means for correcting the target resistance on the basis of the result of the comparison performed by the comparison means.

3. A method of controlling a gas sensor apparatus which includes a gas sensor having at least one cell composed of a solid electrolyte member and a pair of electrodes, the gas sensor outputting a detection signal corresponding to the concentration of a specific gas contained in exhaust gas, and resistance detection means for detecting the internal resistance of the cell, and which is applied to an internal combustion engine for which air-fuel-ratio feedback control is performed on the basis of the detection signal, the method comprising:

an obtaining step of obtaining the detection signal output from the gas sensor;
   a determination step for determining whether or not the value of the detection signal obtained in the obtaining step has reached a start determination value at which the air-fuel-ratio feedback control can be started;
   a start-time resistance detection step, performed when the value of the detection signal is determined in the determination step to have reached the start determination value, for detecting the internal resistance of the cell, as a start-time internal resistance, through use of the resistance detection means; and
   a comparison step of comparing the start-time internal resistance detected in the start-time resistance detection step with a deterioration determination value set in advance,
   wherein the start determination value is a value reached by the detection signal prior to the gas sensor entering an activated state at which time the detection signal becomes stable.

4. A method of controlling a gas sensor apparatus according to claim 3, wherein
   the gas sensor further comprises a heater for heating the solid electrolyte member when energization means supplies electricity to the heater; and
   the method further comprises a determination step of determining the amount of electricity supplied to the heater by the energization means such that the internal resistance detected by the resistance detection means coincides with a target resistance, and a correction step of correcting the target resistance on the basis of the result of the comparison performed in the comparison step.

* * * * *